US011530384B2

(12) United States Patent
Bakkar et al.

(10) Patent No.: US 11,530,384 B2
(45) Date of Patent: Dec. 20, 2022

(54) USE OF MATRIX CELLS FOR PREPARING A MICRO HAIR FOLLICLE (71) Applicant: L'OREAL, Paris (FR)

(72) Inventors: Khalid Bakkar, Aulnay-sous-Bois (FR); Christine Collin-Djangone, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/761,158

(22) PCT Filed: Sep. 28, 2016

(86) PCT No.: PCT/EP2016/073127
§ 371 (c)(1),
(2) Date: Mar. 19, 2018

(87) PCT Pub. No.: WO2017/055358
PCT Pub. Date: Apr. 6, 2017

(65) Prior Publication Data
US 2018/0258390 A1 Sep. 13, 2018

(30) Foreign Application Priority Data
Sep. 29, 2015 (FR) ...................................... 1559186

(51) Int. Cl.
C12N 5/071 (2010.01)
A61K 35/36 (2015.01)
G01N 33/50 (2006.01)

(52) U.S. Cl.
CPC ............ *C12N 5/0628* (2013.01); *A61K 35/36* (2013.01); *C12N 5/0627* (2013.01); *C12N 5/0629* (2013.01); *G01N 33/5044* (2013.01); *C12N 2500/30* (2013.01); *C12N 2500/32* (2013.01); *C12N 2500/84* (2013.01); *C12N 2501/11* (2013.01); *C12N 2501/33* (2013.01); *C12N 2501/39* (2013.01); *C12N 2501/395* (2013.01); *C12N 2501/727* (2013.01); *C12N 2513/00* (2013.01)

(58) Field of Classification Search
CPC .. C12N 5/0628; C12N 5/0627; C12N 5/0629; C12N 2513/00; A61K 35/36
See application file for complete search history.

(56) References Cited

U.S. PATENT DOCUMENTS

2005/0089512 A1* 4/2005 Schlotmann .......... C12N 5/0627
424/93.7
2011/0086079 A1* 4/2011 Lindner .................. A61P 17/14
424/422
2012/0269781 A1 10/2012 Ra et al.
2014/0370070 A1* 12/2014 Lindner .............. A61L 27/3604
424/423

FOREIGN PATENT DOCUMENTS

EP  1 878 790 A1  1/2008
EP  2 274 419 A1  1/2011
WO  WO 95/01423 A1  1/1995
WO  WO 2007/109223 A2  9/2007
WO  WO-2011056017 A2 *  5/2011  .............. A61P 17/14

OTHER PUBLICATIONS

Moll et al., Histochem. Cell Biol., 129:705-733 (2008) (Year: 2008).*
Duchstein et al., Chem. Chem. Phys., 17:21880-21884 (2015) (Year: 2015).*
Hirobe, Dermatol. Sinica, 32:200-204 (2014) (Year: 2014).*
Vogt et al., Hair Growth and Disorders, Chapter 1 (2008) (Year: 2008).*
Guo et al., Cell. Reprog., 17(1):77-87 (2014) (Year: 2014).*
Hwang et al., Develop., 135(18):3149-3159 (2008) (Year: 2008).*
Rogers et al., Int. J. Dev. Biol. 48: 163-170 (2004) (Year: 2004).*
Sasahara et al., Int. J. Oncol., 34:1191-1199 (2009) (Year: 2009).*
Wagner et al., BMC Proceedings, 7(6):P93 (2013) (Year: 2013).*
Mahjour et al., Tiss. Eng. B, 18(1):15-23 (2012) (Year: 2012).*
Horland et al., BMC Proceed., 5(S8)1-2 (2011) (Year: 2011).*
Schneideretal, Current Biology, 19:R132-R142 (2009) (Year: 2009).*
Yang et al., "Review of hair follicle dermal cells", Journal of Dermatological Science, 57 (2010) 2-11.
Thibaut et al., "Hair keratin pattern in human hair follicles grown in vitro", Experimental Dermatology, 2003, 12: 160-164.
Lindner et al, "De novo formation and ultra-structural characterization of a fiber-producing human hair follicle equivalent in vitro", Journal of Biotechnology, Nov. 22, 2011, 152, 108-112.
Blanpain et al, "Self-renewal, multipotency, and the existence of two cell populations within an epithelial stem cell niche", Cell, Sep. 3, 2004, vol. 118, 635-648.
Balana, "Epidermal stem cells and skin tissue engineering in hair follicle regeneration", World Journal of Stem Cells, May 26, 2015, vol. 7, No. 4, 711-727.
Ohyama et al, "Hair follicle bulge: A fascinating reservoir of epithelial stem cells", Journal of Dermatological Science, 2007, vol. 46, No. 2, 81-89.
Yang et al. Upper Human Hair Follicle Contains a Subpopulation of Keratinocytes with Superior In Vitro Proliferative Potential. J. Invest. Dernnatol. 101:652-659 (Year: 1993).
Lavker et al. Hair Follicle Stem Cells. JID Symposium Proceedings 8:28-38 (Year: 2003).
Hilmi et al. A simple culture method for epithelial cells derived from human hair follicle, Cent.Eur. J. Biol 8(5): 432-439, (Year 2013).
Roh et al. Dermal papilla-induced hair differentiation of adult epithelial stem cells from human skin. Physiol Genomics 19: 207-217 Year: 2004).

(Continued)

*Primary Examiner* — Lynn Y Fan
(74) *Attorney, Agent, or Firm* — Polsinelli PC (57) ABSTRACT The invention relates to the use of matrix cells for obtaining a micro hair follicle and to the use thereof for evaluating the effect of cosmetic, pharmaceutical or dermatological products and also for the prophylactic or therapeutic treatment of a state of reduced pilosity.

16 Claims, 12 Drawing Sheets (56) References Cited

OTHER PUBLICATIONS

Roh et al. In Vitro Differences Between Keratinocyte Stem Cells and Transit-Amplifying Cells of the Human Hair Follicle. J Invest Dermatol 125:1099-1105 (Year: 2005).

Chacon-Martinez et al. Hair follicle stem cell cultures reveal self-organizing plasticity of stem cells and their progeny. The EMBO Journal (2017) 36: 151-164 (Year: 2017).

Inoue et al. Differential expression of stem-cell-associated markers in human hair follicle epithelial cells. Laboratory Investigation 2009) 89, 844-856 (Year: 2009).

\* cited by examiner

USE OF MATRIX CELLS FOR PREPARING A MICRO HAIR FOLLICLE

CROSS REFERENCE TO RELATED APPLICATIONS

This application is a National Phase filing under 35 U.S.C. § 371 of PCT/EP2016/073127 filed on Sep. 28, 2016; and this application claims priority to Application No. 1559186 filed in France on Sep. 29, 2015 under 35 U.S.C. § 119. The entire contents of each application are hereby incorporated by reference.

The present invention relates to a process for producing a micro hair follicle by culture and amplification of matrix cells.

It likewise relates to the micro hair follicles produced by means of the process mentioned above and to the use thereof for treating alopecia and also for evaluating the effect of cosmetic, pharmaceutical and dermatological products.

Alopecia is conditioned by various factors: genetic, hormonal and environmental, by the diet and by physical activity. The hair has an essential aesthetic and identity role. Alopecia in women or in men can thus be responsible for considerable psychological suffering.

Thus, healthy, strong hair and a dense head of hair throughout one's lifetime is an ambition of most women and men.

Many techniques are known for treating alopecia, such as cell therapy, laser therapy or else implants without surgery. The latter gives an immediate result and is much less invasive than surgery.

In order to obtain implants, human hair follicles are obtained by culturing various cell types present in the hair bulb.

The hair bulb is pear-shaped and it is composed:
- of the papilla which is a budding of dermal origin, located at the base of the follicle. It is a highly vascularized site which participates in the nutrition and regulation of the growth of the hair through its store of growth factors and extracellular matrix proteins. This information will be transmitted to the matrix cells, produced in the matrix, to allow differentiation thereof (Rees J L. Genetics of hair and skin color; Voyage 3D au Coeur du cheveu [3D voyage to the Heart of the hair] web site—URL: www.hair-science.com);
- of the matrix which is a zone capping the dermal papilla, constituted of a clump of matrix cells which are not very differentiated. It is the seat of intense mitotic activity. The matrix cells, which are located in the hair bulb and which form a small cell clump around the dermal papilla, are mainly constituted of precursors of keratinocytes which constitute a germinative stratum and which proliferate rapidly so as to differentiate to form the hair shaft, thus playing an essential role in the hair cycle. From the beginning of the anagen phase up to the end of said phase, these matrix cells will proliferate up to the catagen phase and then disappear in the telogen phase. (Ebling F J. The biology of hair. Dermatol Clin. 1987 July; 5(3):467-81. Review; Saitoh M, Uzuka M, Sakamoto M. Human hair cycle. J Invest Dermatol. 1970, January 54, pages 65-32. Cell differentiation will allow the formation of the various cell types of the outer epithelial sheath (ORS), of the inner epithelial sheath (IRS) and then of the hair shaft. It is also this matrix which conditions the shape of the hair. The matrix is distributed uniformly about an axis of symmetry for straight hair, whereas it will be greater on one side for curly hair (Voyage 3D au Coeur du cheveu [3D voyage to the Heart of the hair] web site—URL: www.hair-science.com; Melissopoulos A and Levacher C. Les annexes cutanées [The skin appendages]. In: La peau: structure et physiologie [The skin: structure and physiology], published by Lavoisier; 1998. P. 57-99). The matrix also comprises follicle melanocytes which are responsible for the pigmentation of the hair. The proliferation and differentiation of these matrix cells are controlled by the dermal papilla (Botchkarev V A, Kishimoto J. Molecular control of epithelial-mesenchymal interactions during hair follicle cycling. J Invest Dermatol Symp Proc. 2003 June; 8(1):46-55. Review);
- of the outer and inner epithelial sheaths which are produced by the upper matrix of the hair bulb, also known as the keratinization zone. The outer epithelial sheath constitutes the outer envelope of the follicle: it is an invagination of the epidermis. It houses in particular stem cells from which the hair follicle will be cyclically regenerated. The inner epithelial sheath separates the outer epithelial sheath from the hair shaft. This sheath is constituted of three cell types organized in keratinized concentric layers which accompany the growth of the hair. Henlé's layer, Huxley's layer and the cuticle which is formed from flattened cells, directed towards the hair matrix, are distinguished;
- of the hair shaft which is partly visible, this is the hair. The structure of the hair shaft is made up of three distinct layers from the outside to the inside. There is the cuticle, the cortex and the medulla, all made up all keratinized cells.

Hair follicles more or less close to the human hair follicle have been developed for several years. Mention may for example be made of hair follicles obtained by culturing various cells of the hair bulb, described in the following documents: EP 2 274 419, EP 2 447 357.

Nevertheless, none of these models contains matrix cells, which are the cells essential for formation of the hair shaft, in sufficient amount to represent most of the characteristics of a human micro follicle.

Surprisingly, the applicant has demonstrated that culturing the cells of the matrix in the presence of Y27632 allows considerable proliferation of these cells and differentiation thereof into keratinocytes that are positive for the K85 K35 markers, which reach confluence while forming regular clusters.

These cells placed in 3D culture, make it possible to obtain, unexpectedly, a micro hair follicle exhibiting most of the characteristics of a microfollicle in vivo, comprising in particular keratinocytes and melanocytes. The cells forming this hair follicle exhibit the characteristic of expressing the k85 k35 markers.

The process, according to the invention, thus proves to be advantageous due to the fact that it makes it possible to obtain a microfollicle by using a single cell type, that of the matrix cells, which provides all the cell types required for the formation of a micro hair follicle.

Thus, according to a first of its subjects, the present invention relates to the use of the matrix cells for preparing a micro hair follicle.

Use of Matrix Cells for Preparing a Micro Hair Follicle

The term "matrix cells" is intended to mean the cells located in the hair bulb and which form a small cell clump around the dermal papilla (Ebling F J. The biology of hair. Dermatol Clin. 1987 July; 5(3):467-81. Review; Saitoh M, Uzuka M, Sakamoto M. Human hair cycle. J Invest Dermatol. 1970

January; 54(1):65-81). Samples of these cells may be taken, and they may be amplified and stored in tissue libraries for the purpose of subsequent use.

In order to preserve the integrity of the matrix tissue, these cells may be sampled according to the process which follows: hair follicles are placed in a Petri dish containing a minimum culture medium supplemented with 2% of antibiotic and non-essential amino acids.

The bulb region is cut at the top of the dermal papilla and the epithelium of the bulb is thus separated from the dermal papilla and from the connective tissue sheath. The matrix cells provide all the cells required for the preparation of a micro hair follicle and, thus, the use of matrix cells for preparing a micro hair follicle requires no other cell type and may be carried out without the provision of any exogenous cells.

In order to obtain a sufficient amount of matrix cells for obtaining a micro hair follicle, the applicant has developed a method of amplifying these cells so that they differentiate into K 85 K 35 keratinocytes forming clusters once at confluence.

Thus, the applicant has developed a process for preparing a micro hair follicle, comprising at least one step of amplifying the matrix cells in the presence of an effective amount of a ROCK inhibitor for a period of time sufficient to allow differentiation of said cells into keratinocytes positive for the K85 K35 markers.

This process for preparing the micro hair follicle is characterized in that it comprises the following steps:
 a—isolating a follicle from a scalp sample;
 b—cutting, on said support immersed in a culture medium, the bulb region above the dermal papilla;
 c—separating the matrix cells in the form of a cell aggregate from the connective tissue sheath and from the dermal papilla;
 d—depositing the cell aggregate on a feeder layer of 3T3i fibroblasts, blocked with mitomycin, in a green 7F medium;
 e—amplifying the matrix cells at the surface of said support in the presence of a ROCK inhibitor;
 f—recovering the K85 K35 keratinocytes;
 g—culturing the keratinocytes obtained in step f) in 3D culture.

Microdissection

The matrix cells can only be sampled from a hair in the anagen phase.

The region of the matrix contains a very small number of cells.

Thus, one difficulty to be overcome lies in the obtaining of matrix cells of quality and in sufficient amount.

This is because, under normal conditions, when a hair falls out or after it has been pulled out, the dermal papilla-matrix cell compartment remains in the dermis of the scalp. This compartment will initiate the development of a new hair cycle and will give a new microfollicle again.

Thus, pulling out a hair does not make it possible to obtain these matrix cells; it will therefore be necessary to perform a scalp biopsy, and then to isolate these cells by microdissection.

According to the invention, the matrix cells are obtained by means of a novel microdissection technique which preserves the amount and the integrity of the cells, since they are not separated from one another. This is because the microfollicle is isolated on a support, the bulb region is cut above the dermal papilla and the matrix cells are recovered in the form of a cell aggregate on the same support. This microdissection makes it possible to isolate and preserve all of the matrix cells.

Amplification

In addition to being difficult to isolate, the matrix cells are also difficult to culture at least for the following reasons:
 a) the number thereof is particularly low;
 b) they dissociate easily and it is therefore difficult to pinpoint them during the microdissection;
 c) they do not adhere to a plastic support;
 d) they are difficult to amplify pure since they are often contaminated with fibroblasts from the dermal papilla or from the connective tissue sheath.

Some authors have proposed culturing these cells in coculture with papilla fibroblasts. The drawback of this method is that the culture obtained is not homogeneous, the matrix cells are contaminated with the dermal fibroblasts from the papilla used in coculture (Reynolds A J, Lawrence C M, Jahoda C A Human hair follicle germinative epidermal cell culture. J Invest Dermatol. 1993 October; 101(4):634-8).

Luo et al. have proposed a technique of microdissection followed by culture of the matrix cells on a plastic support (Luo et al: Methods for culturing hair follicle epithelial matrix cells; Reg. number: H1610; Nov. 5, 1996). However, this microdissection technique results in a very low yield of matrix cells.

The applicant has isolated the matrix cells and developed a process for culturing these cells. Specifically, in the presence of the Y27632 growth factor, which is a ROCK inhibitor, these cells proliferate rapidly and differentiate into K85 K35 keratinocytes until they reach confluence while forming regular clusters.

The cells are amplified according to the technique of Rheinwald and Green (Cell, vol. 6, 331-344,1975) by culturing on a feeder support constituted of fibroblasts in a suitable medium known to those skilled in the art, in the presence of growth factors, in particular amino acids, serum, cholera toxin, insulin, triiodothyronine and pH buffer solution. In particular, such a culture medium may in particular contain at least one mitogenic growth factor for keratinocytes (for example epidermal growth factor (EGF) and/or keratinocyte growth factor (KGF), in particular KGF), insulin, hydrocortisone and optionally an antibiotic (e.g.: gentamycin, amphotericin B) to which a ROCK inhibitor, Y27632, has been added.

Advantageously, said medium may also comprise serum or a pituitary extract, for example of bovine origin, epinephrine, transferrin and/or non-essential amino acids.

The fibroblasts used for this culture will more preferentially be 3T3 fibroblasts. 3T3 fibroblasts are well known to those skilled in the art. It is a fibroblast cell line that has been known since 1962. "3T3" means "3-day transfer, inoculum of $3 \times 10^5$ cells".

The cell culture is preferably a culture on fibroblasts (preferentially 3T3 fibroblasts), the proliferation of which has been stopped beforehand, preferentially by having previously irradiated them (for example with UV radiation) or previously treated them with mitomycin. Mitomycin (in particular mitomycin C) blocks the proliferation of these cells without however preventing them from producing nutritive substances useful for keratinocyte proliferation.

With this technique, the matrix cells proliferate on the support on which they have been separated from the other cell types. This makes it possible to preserve a sufficient number of matrix cells. The cells proliferate rapidly in the presence of Y27632 up to confluence and differentiate into cells that are positive for the early hair keratin markers K35 and K85, while forming regular clusters.

According to the invention, the term "effective amount" denotes an amount required to obtain a culture of K85 K35 keratinocytes at confluence.

According to the invention, the effective amount of the ROCK inhibitor, Y27632, is between 1 and 100 μM and preferably between 5 and 25 μM and preferably 10 μM.

According to the invention, the matrix cells are cultured in the presence of the ROCK inhibitor, Y27632, for at least 2 days and preferably for at least 3 days.

The term "clusters" is intended to mean a clump of cells grouped together.

The term "at confluence" is intended to mean a cell layer having no interstice between each adherent cell cultured in monolayer on an appropriate support.

Culturing of K35 and K85 Differentiated Cells in 3D Culture to Obtain a Micro Hair Follicle The keratinocytes positive for the K35 and K85 markers, forming regular clusters once at confluence, are recovered by enzymatic treatment.

The 3D spheres are obtained on 96-well microplates of Insphero type by the hanging drop method or method with microplates for culturing non-adherent cells (GravityPLUS White paper system).

The cells are then cultured in a green medium at 37° C.; the appearance of the micro hair follicle is observed after at least 5 days of culture.

According to one embodiment, the cells are maintained in culture for at least 2 days and preferably at least 5 days.

Preferably, the number of cells placed in culture is between 1000 and 4000 cells and is preferably 3000 cells.

Another subject of the invention is a micro hair follicle that can be obtained by means of the process according to the invention.

These micro hair follicles make it possible to use them for the prophylactic or therapeutic treatment of a state of reduced pilosity, in particular alopecia, and constitute predictive tests for the activity of cosmetic and/or pharmaceutical active agents or else side effects of topical ingredients.

Prophylactic or Therapeutic Treatment of a State of Reduced Pilosity, in Particular Alopecia Given that the micro hair follicle has the characteristics of a hair follicle in vivo, it may be used as an implant, optionally combined with skin substitutes.

The micro hair follicle according to the invention will therefore also have uses for preparing implants and/or a skin substitute for treating a skin disorder such as a burn, a healing defect or hair that has turned white or grey.

A therapeutic effect is defined as a return to the normal state of pilosity, whether totally or partially.

For the purposes of the invention, prophylactic treatment is recommended if the subject has a prior condition for hair loss, such as a familial disposition.

The conditions of a reduced amount of hair may be the result of alopecia, hereditary baldness, scars, burns or accidental injuries.

Predictive Tests for the Activity of Cosmetic and/or Pharmaceutical Active Agents The micro hair follicle equivalents according to the invention will make it possible to perform in particular time courses of body hair or head hair growth and therefore any study requiring numerous hairs that are alive and as complete as possible in an in vivo context such as the study of the hair cycle and of the factors capable of influencing this cycle, ranging up to the study of active agents which promote hair growth, of active agents which make it possible to combat hair loss or else of active agents which slow down body hair growth.

The product screening processes for the purpose of identifying novel active agents comprise a step (a) of bringing said test product into contact with a scalp equivalent according to the invention, then a step (b) of analysing the effect of said product on at least one parameter of the scalp equivalent and a step (c) of selecting the product which modifies said parameter.

Preferably, for carrying out step (a), the test product is applied topically, for example, formulated in conventional topical formulations or else introduced into the culture medium.

Step (b) may, in particular, be carried out by analysing the expression, the production and/or the activity of markers associated with the quality and/or with the homeostasis of the micro hair follicle, for instance epidermal and/or dermal markers, such as structural proteins. As an example of structural proteins, mention may be made of the hair keratins.

For this, the effect of the product on the growth of the hair shaft will be analysed in step (b) of the screening process. Step (b) of analysing the effect of the product will preferentially be a comparison of at least one parameter measured on the micro hair follicle brought into contact with the test product with that or those measured on a control micro hair follicle cultured under the same conditions but which has not received the test product.

Step (c) of selecting the product which modifies the parameter of the scalp equivalent will be carried out as a function of a criterion determined beforehand.

The modification of this parameter may be a stimulation, a decrease or a total or partial inhibition of the expression, of the production and/or of the activity of said markers and/or of the growth of the hair shaft.

The criterion for selecting said product will for example be that this product has a stimulatory or inhibitory effect on the parameter measured.

The scalp equivalent according to the invention can also be used in automated processes for screening cosmetic, pharmaceutical or dermatological compounds for identifying novel active agents.

DESCRIPTION OF THE FIGURES

The figures make it possible to give a better illustration of the invention, without however limiting the scope thereof.

EXAMPLE 1—PREPARATION OF A MICRO HAIR FOLLICLE

Experimental Protocol i. Matrix Cell Microdissection

The hair follicles are extracted from a surgical residue of scalp. Said residue is first cut into 5 mm² portions and then sectioned using a scalpel between the dermis and the hypodermis.

Figure 1:
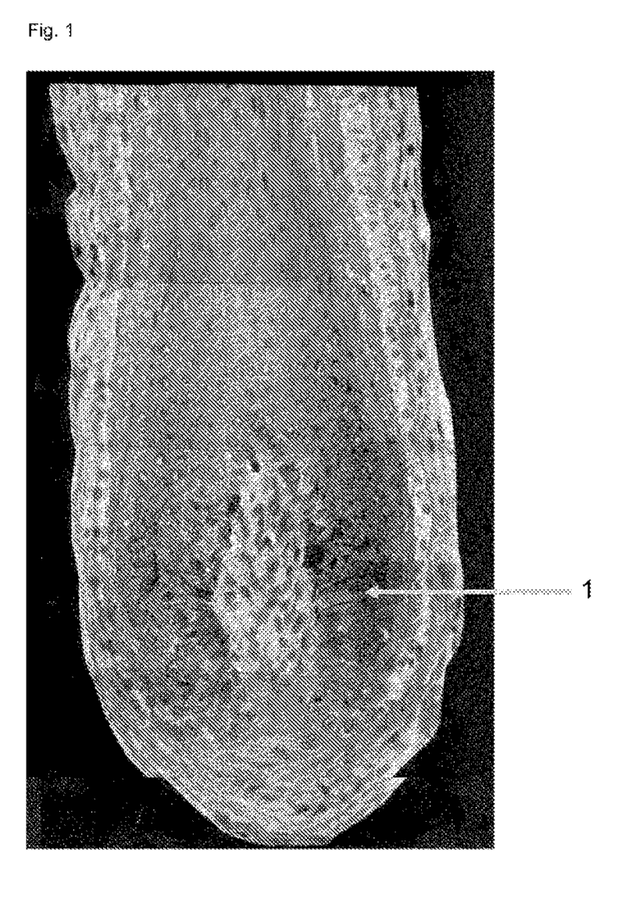
FIG. 1: Matrix cell 1 localization
Figure 2:
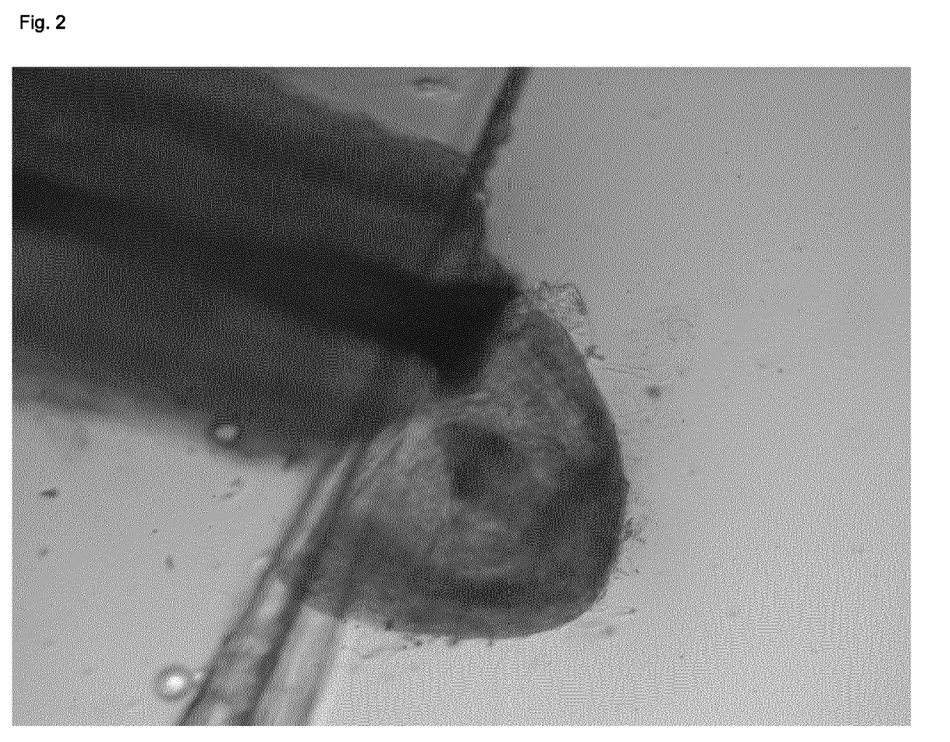
FIG. 2: Section above the dermal papilla
Figure 3:
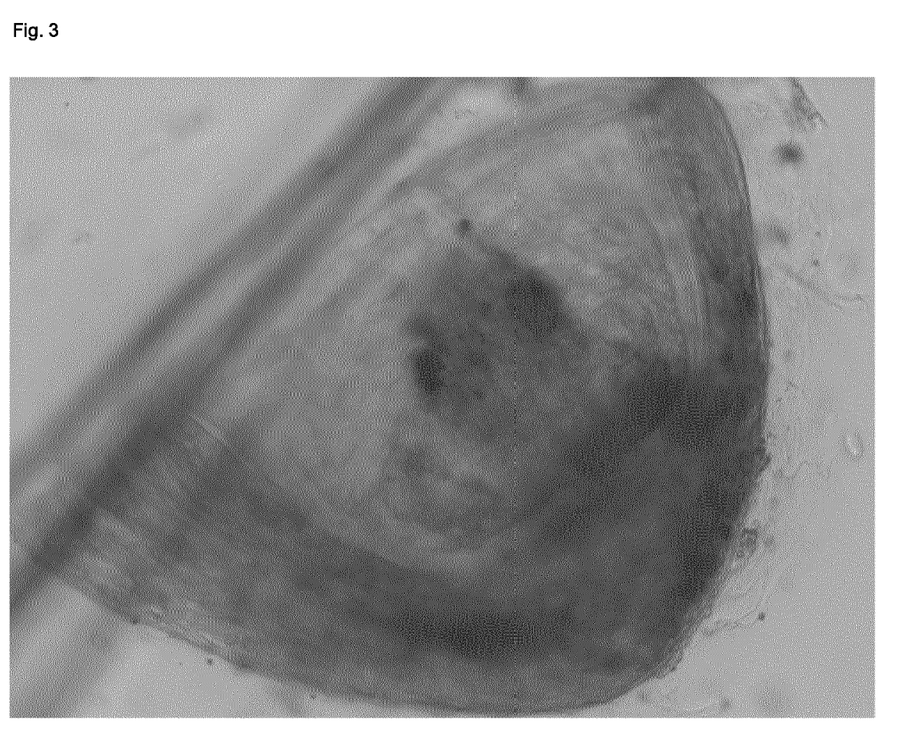
FIG. 3: Bulb containing the matrix cells

The follicles are extracted using ophthalmic surgery forceps and are then sectioned just above the papilla with a scalpel (FIG. 2). The bulb is then recovered (FIG. 3). At this stage, the bulb comprises two compartments: The dermal compartment (dermal papilla and connective tissue sheath). The matrix cells which form a cell mass.

The epithelial part is separated from the dermal part using perfusion needles.

ii. Culture Conditions:

The culture conditions have three main components:

The base medium:

Unless otherwise indicated, all of the media and buffers used in the examples are described in Bell et al. 1979, (P.N.A.S. USA, 76, 1274-1278), Asselineau and Prunieras, 1984, (British J. of Derm., 111, 219-222) or Asselineau et al., 1987, (Models in dermato., vol. III, Ed. Lowe & Maibach, 1-7). The MEM medium+10% FCS+3F (called 3F medium) has the following composition:

| MEM | Final concentrations |
|---|---|
| Foetal calf serum (FCS) | 10% |
| L-Glutamine | 2 mM |
| Sodium pyruvate | 1 mM |
| Penicillin - Streptomycin | Penicillin 20 U/ml |
| | Streptomycin 20 µg/ml |
| Fungizone | Penicillin 10 U/ml |
| | Streptomycin 10 µg/ml |
| | Amphotericin-B 25 ng/ml |
| Epidermal growth factor (EGF) | 10 ng/ml |
| Cholera toxin | $10^{-10}$ M |
| Hydrocortisone | 0.4 µg/ml |
| Adenine hydrochloride | $1.8 \times 10^{-4}$ M |
| Triiodothyonine (T3) | $2 \times 10^{-9}$ M |
| Human transferrin | 5 µg/ml |
| Bovine insulin | 5 µg/ml | the culture supplements: growth factors which signal to the cell that it must divide or differentiate. 10 µM of Y27632.

the adhesion surface: the matrix cells adhere and proliferate in the Green-based medium in the presence of a feeder layer of murine 3T3 fibroblasts arrested in the cell cycle by mitomycin treatment.

Culture-Amplification of Keratinocytes

After microdissection, the matrix cell clumps are deposited in Petri dishes 60 mm in diameter, seeded beforehand with 1 million 3T3 cells, and covered with the complete culture medium; a culture of matrix cells at confluence is obtained. In order to generate the spheres, the cells are recovered at the subconfluent stage by enzymatic treatment. The spheres can be obtained in various ways with the conventional techniques already described (hanging drop, centrifugation, non-adhesive support). In the case of the hanging drop, 3000 cells are placed in the plates in sphero. They are recovered in 96-well plates after 48 h in order to monitor their progression.

Figure 4:
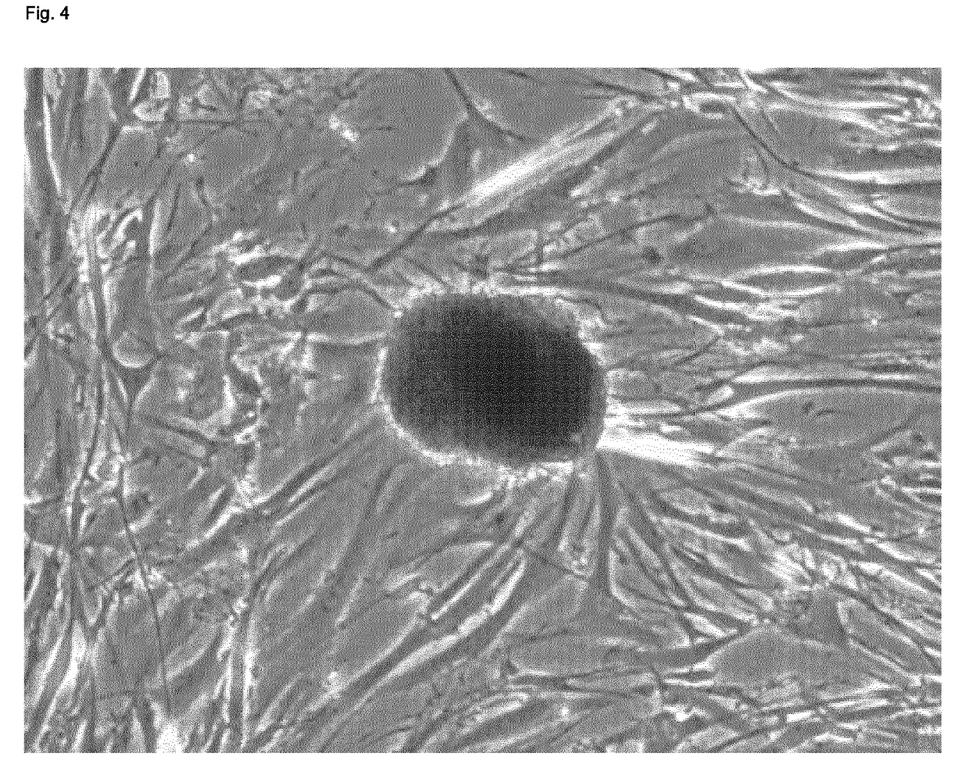
FIG. 4: Matrix cell clump deposited on a 3T3 feeder layer
Figure 5:
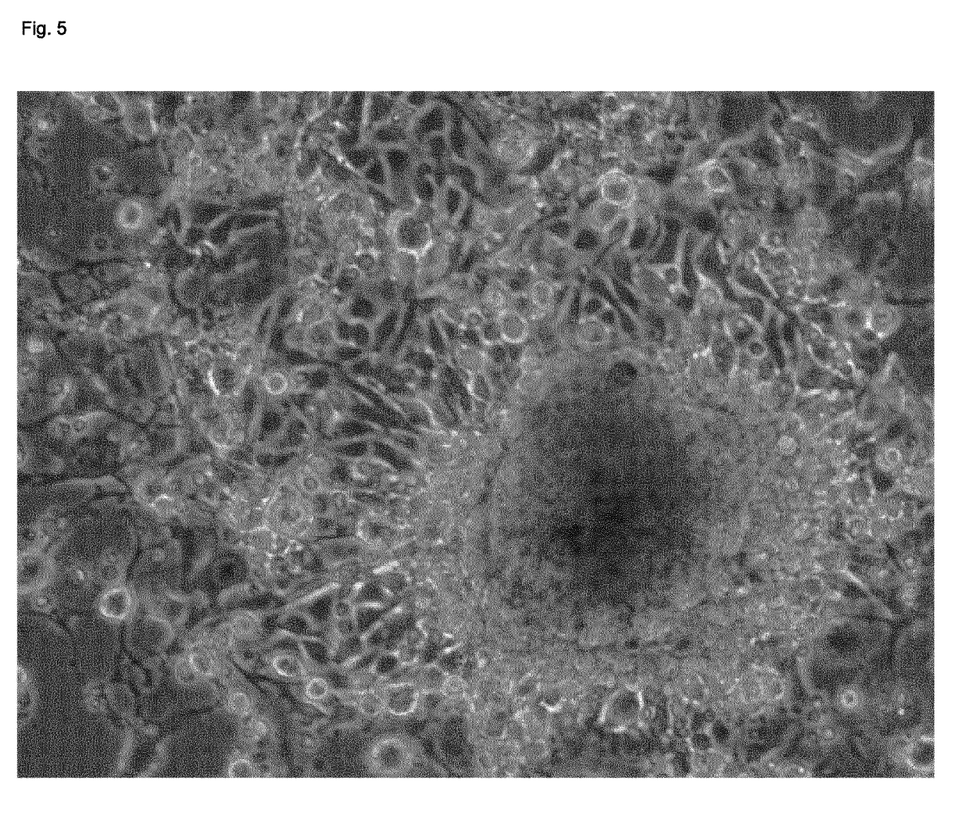
FIG. 5: Matrix cells after 3d of culture
Figure 6:
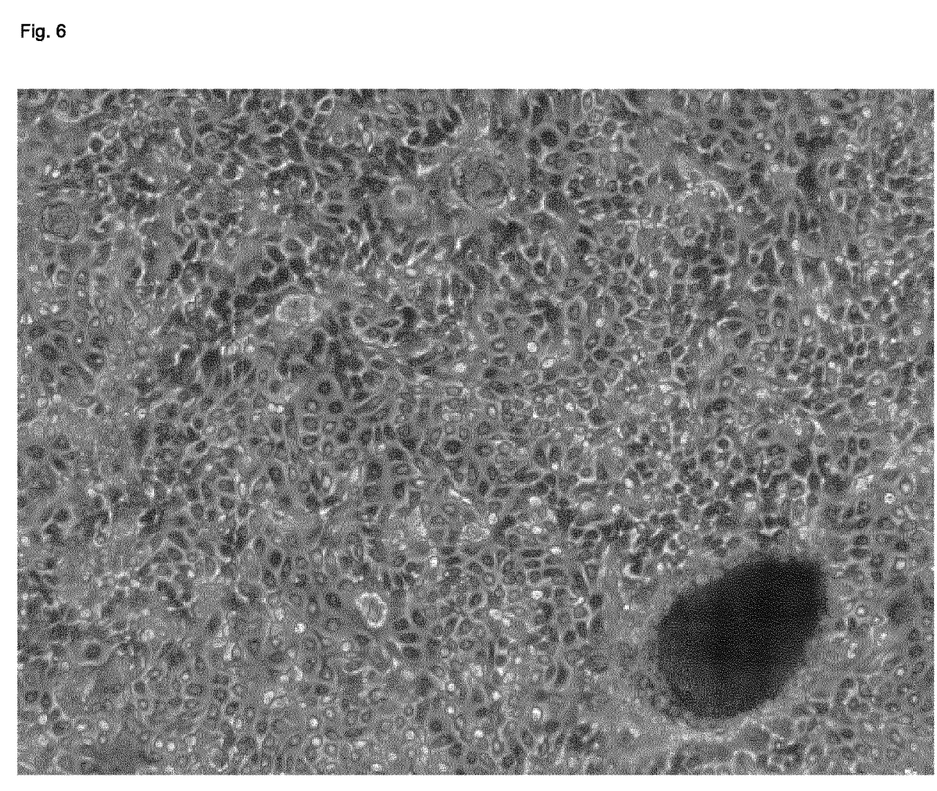
FIG. 6: Matrix cells at confluence after 10 days of culture

The non-dissociated matrix cell clumps are isolated and deposited on a 3T3 feeder layer (FIG. 4). After 3d of culture, the cells begin to proliferate in the form of a colony around the matrix clump (FIG. 5). The cells reach subconfluence in 10 days (FIG. 6). They are characterized by a very small size and a strong proliferative capacity. In order to ensure amplification, the cells are then seeded into a T75 flask. Thus, after 3 weeks of culture of 3 bulbs, it is possible to generate approximately 40 million matrix cells at passage 1.

Figure 7:
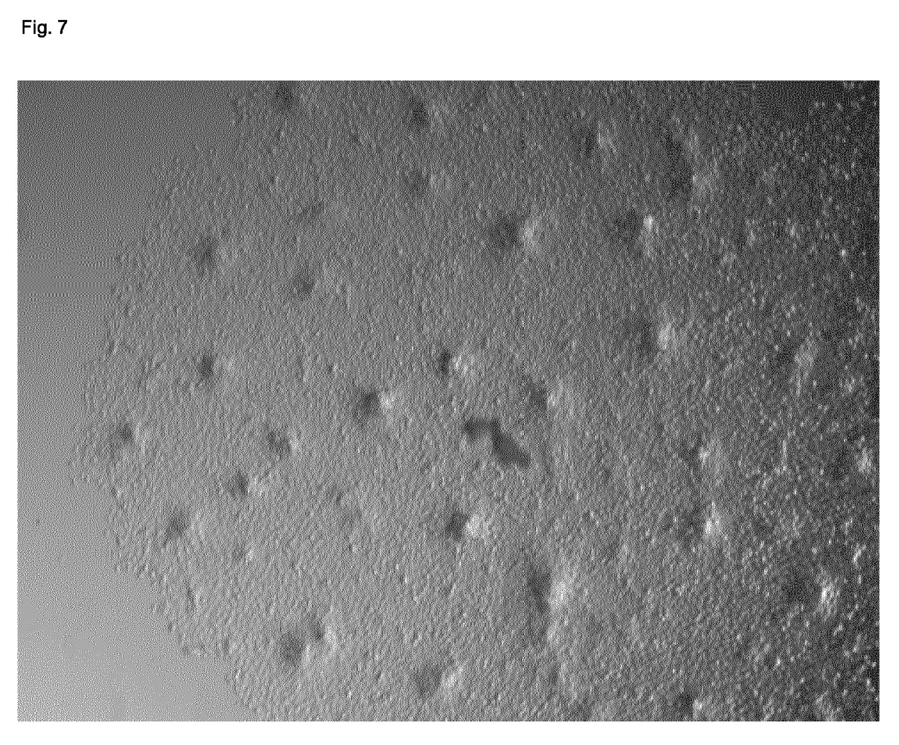
FIG. 7: Primary culture of matrix cells with cluster formation

It was possible to observe that the matrix cells were capable of very rapidly forming cell aggregates in vitro. This phenomenon appears to be due to the taxis properties of these cells. In the green 7F medium, these clumps form a regular pattern which recalls that of the follicle buds (FIG. 7).

Furthermore, during the formation of these clumps, the production of numerous spherical cells in suspension occurs, and said cells can be subcultured to generate new cell cultures. After characterization, the buds represent a 1st phase of differentiation of the matrix cells and they are positive for the early keratins of the hair: K35 and K85.

Figure 8:
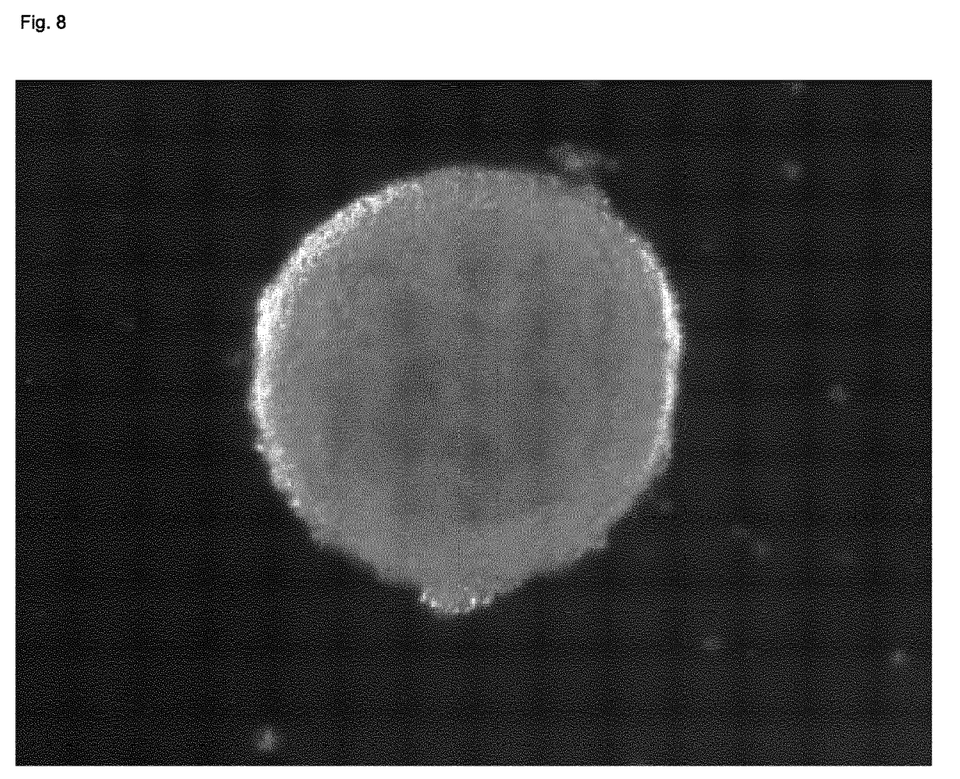
FIG. 8: Sphere of matrix cells after 3d of 3D culture

3D culture with the matrix cells was also carried out. These cells form spheres after 3d of culture (FIG. 8).

Figure 9:
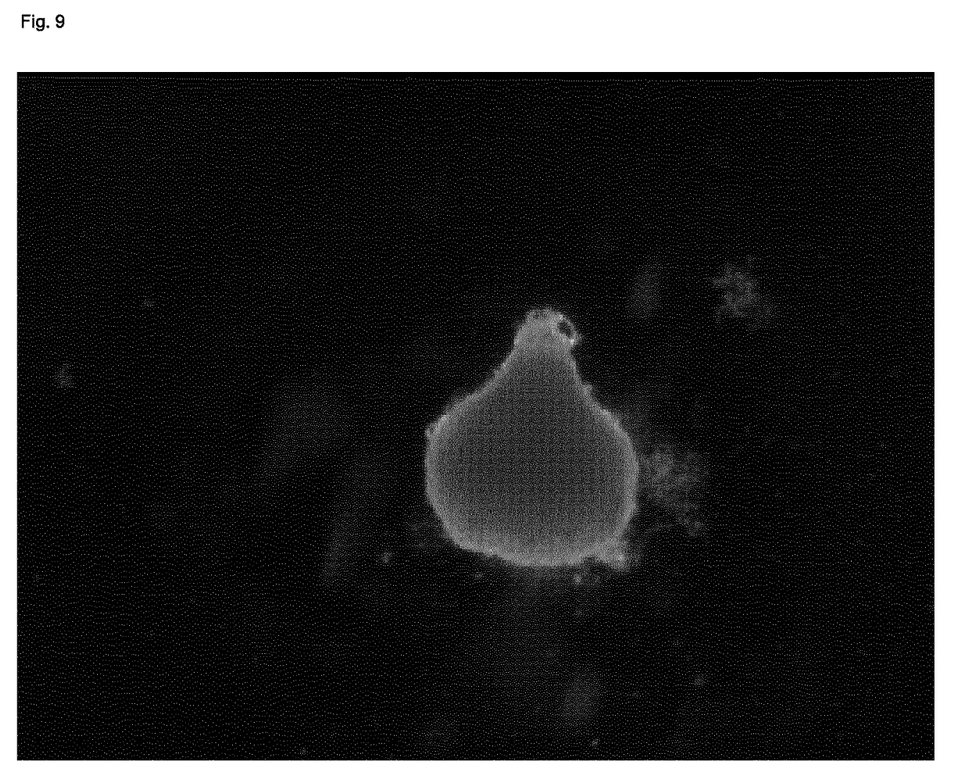
FIG. 9: Bud formation in 3D culture

After some 7 days of culture, these spheres change conformation, showing a polarized organization. A budding appears, which seems to indicate differentiation of the spheres (FIG. 9). These buds are strongly positive for K85 and K35.

Figure 10:
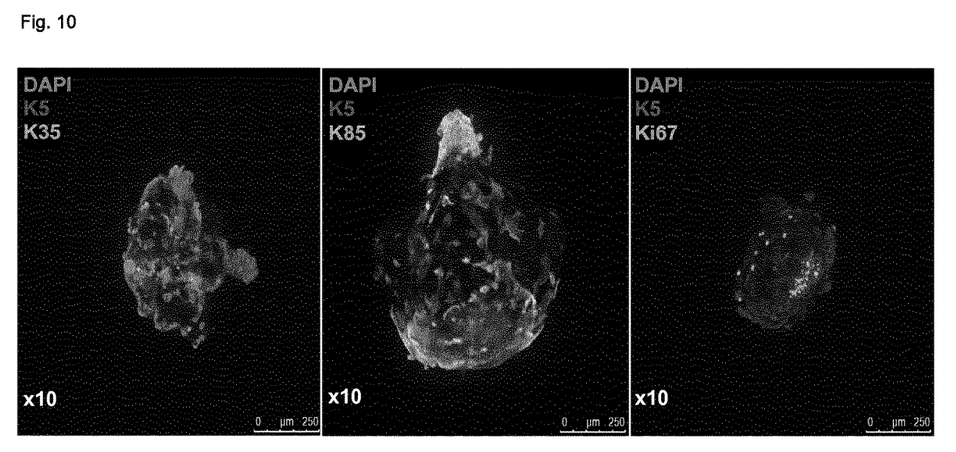
FIG. 10: Buds are strongly positive for K85 and K35
Figure 11:
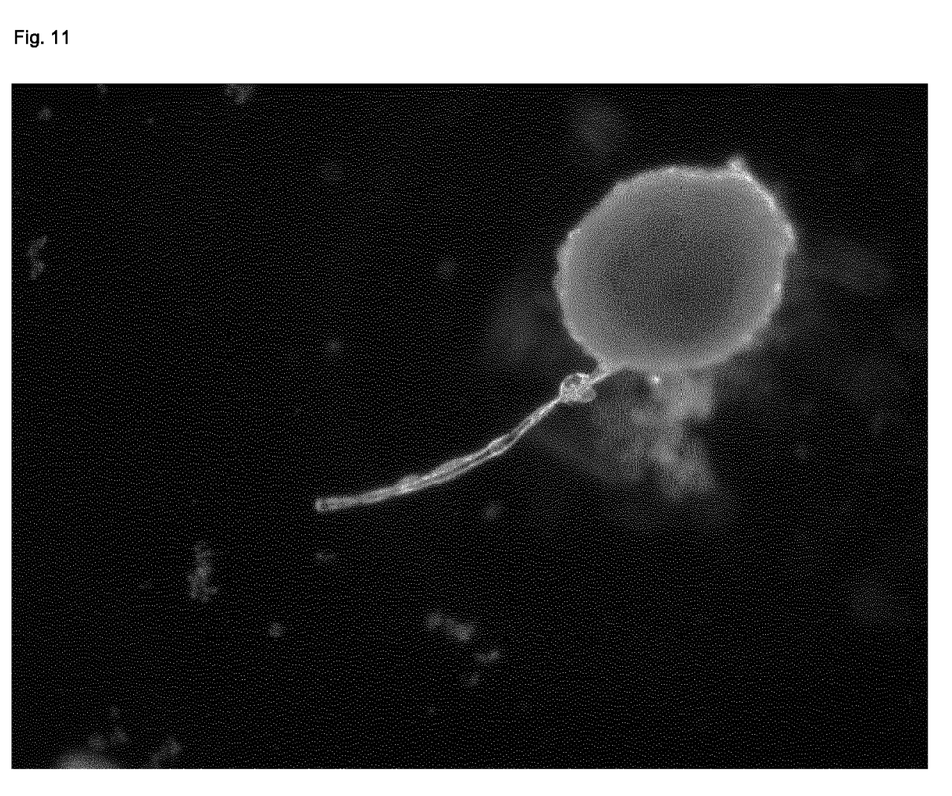
FIG. 11: spheres exhibiting a micro hair follicle
Figure 12:
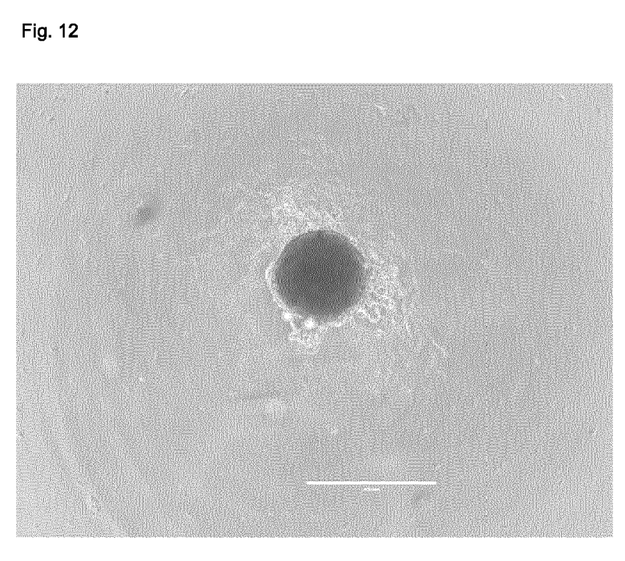
FIG. 12: No bud formation in 3D culture from ORS keratinocytes The examples given below are presented as non-limiting illustrations of the invention.

Some spheres exhibit a structure in the form of a fibre which appears to be keratinized (FIG. 10) and which is not found starting from an ORS keratinocyte culture.

The invention claimed is:

1. One or more micro hair follicles in the form of a bud that is obtained by means of an in vitro process comprising at least one step of culturing matrix cells which are located in the hair bulb in the presence of an effective amount of a ROCK inhibitor for a period of time sufficient to allow differentiation of said cells into keratinocytes positive for the K85 K35 markers, wherein the cells are keratinocytes positive for the K85 K35 markers and upon reaching confluence are in the form regular clusters and wherein the matrix cells are obtained from hair in the anagen phase and are free from other cell types, and wherein at least one bud comprises a structure in the form of keratinized fibre.

2. The one or more micro hair follicles according to claim 1, in which the ROCK inhibitor is Y27632.

3. The one or more micro hair follicles according to claim 1, in which the effective amount of the ROCK inhibitor is from 1 to 100 µM.

4. The one or more micro hair follicles according to claim 1, in which the effective amount of the ROCK inhibitor is from 5 to 25 µM.

5. The one or more micro hair follicles according to claim 1, in which the effective amount of the ROCK inhibitor is 10 µM.

6. The one or more micro hair follicles according to claim 1, in which the matrix cells are cultured in the presence of the ROCK inhibitor for at least 2 days.

7. The one or more micro hair follicles according to claim 1 wherein said process comprises the following steps:
   a—isolating a follicle on a support;
   b—cutting, on said support immersed in a culture medium, the bulb region above the dermal papilla;
   c—recovering the matrix cells in the form of a cell aggregate on said support;
   d—amplifying the matrix cells in the presence of a ROCK inhibitor;
   e—recovering keratinocytes positive for K35 K85 markers;

f—culturing the keratinocytes obtained in step e) in 3D culture.

8. The one or more micro hair follicles according to claim 7, wherein in step f), the number of keratinocytes placed in culture is between 1000 and 4000 cells.

9. The one or more micro hair follicles according to claim 1, which are constituted of cells resulting from amplification and differentiation of matrix cells which are located in the hair bulb in the presence of a ROCK inhibitor.

10. The one or more micro hair follicles according to claim 9, wherein the ROCK inhibitor is Y27632.

11. A process for a prophylactic or therapeutic treatment of a state of reduced pilosity, which comprises implanting the one or more micro hair follicles according to claim 1, into a subject in need of the prophylactic or therapeutic treatment of a state of reduced pilosity.

12. A process for treating alopecia which comprises implanting the one or more micro hair follicles according to claim 1, into a subject having alopecia.

13. A process for the in vitro testing of effects of an active agent on hair properties which comprises contacting the active agent with the one or more micro hair follicles as described in claim 1.

14. The process according to claim 13 further comprises identifying a compound which modulates the growth of body hair and/or of head hair.

15. A product screening process for the purpose of identifying novel active agents, comprising a step (a) of bringing a test product into contact with the one or more micro hair follicles according to claim 1, then a step (b) of analyzing the effect of said product on at least one parameter of a scalp equivalent and a step (c) of selecting the product which modifies said parameter.

16. The one or more micro hair follicles according to claim 2, in which the effective amount of the ROCK inhibitor is from 1 to 100 µM.

* * * * *